United States Patent [19]
Navia et al.

[11] Patent Number: 5,976,069
[45] Date of Patent: Nov. 2, 1999

[54] EPICARDIAL IMMOBILIZATION DEVICE

[75] Inventors: José Antonio Navia; Jorge Luis Jordana, both of Buenos Aires, Argentina

[73] Assignee: Guidant Corporation

[21] Appl. No.: 08/899,829

[22] Filed: Jul. 24, 1997

[51] Int. Cl.$^6$ .................................................. A61F 2/00
[52] U.S. Cl. .......................................... 600/37; 128/897
[58] Field of Search ....................... 100/37; 128/897–99; 623/1–3, 66

[56] References Cited

U.S. PATENT DOCUMENTS

| | | |
|---|---|---|
| 3,411,505 | 11/1968 | Nobis . |
| 4,457,300 | 7/1984 | Budde . |
| 4,637,377 | 1/1987 | Loop . |
| 4,744,363 | 5/1988 | Hasson . |
| 5,339,801 | 8/1994 | Poloyko et al. . |
| 5,415,666 | 5/1995 | Gourlay et al. . |
| 5,425,705 | 6/1995 | Evard et al. . |
| 5,452,733 | 9/1995 | Sterman et al. . |
| 5,536,251 | 7/1996 | Evard et al. . |
| 5,613,937 | 3/1997 | Garrison et al. . |
| 5,782,746 | 7/1998 | Wright ...................................... 600/37 |

FOREIGN PATENT DOCUMENTS

| | | |
|---|---|---|
| 0 791 330 | 8/1997 | European Pat. Off. . |
| 0 820 721 | 1/1998 | European Pat. Off. . |
| WO 95/17127 | 6/1995 | WIPO . |
| WO 96/32882 | 10/1996 | WIPO . |
| WO 97/40738 | 11/1997 | WIPO . |

OTHER PUBLICATIONS

Harlan, Bradley J., M.D., et al., Preparation for Cardiopulmonary Bypass, *Manual of Cardiac Surgery*, Second Edition, pp. 23–32 (1994).

Harlan, Bradley J., M.D., et al., Coronary Artery Surgery, *Manual of Cardiac Surgery*, Second Edition, pp. 84–131 (1994).

Borst, et al. Coronary Artery Bypass Grafting Without Cardiopulmonary Bypass and Without Interruption of Native Coronary Flow Using a Novel Anastomosis Site Restraining Device ("*Octopus*"), vol. 27, No. 6 (May 1996).

CTS (CardioThoracic Systems) MIDCAB™ System (*Platform, Stabilizer, LIMA–Lift™, LIMA–Loop™* Brochure (1996).

*Primary Examiner*—John P. Lacyk
*Attorney, Agent, or Firm*—Fenwick & West LLP

[57] ABSTRACT

A device and method for immobilizing a portion of the epicardium without interrupting the beating of the heart, which includes a frame that can be temporarily anchored to the epicardium and one or more expandable members attached to the frame which, upon inflation, temporarily occlude the passage of blood through the vessel or vessels in the operational field defined by the frame.

23 Claims, 3 Drawing Sheets

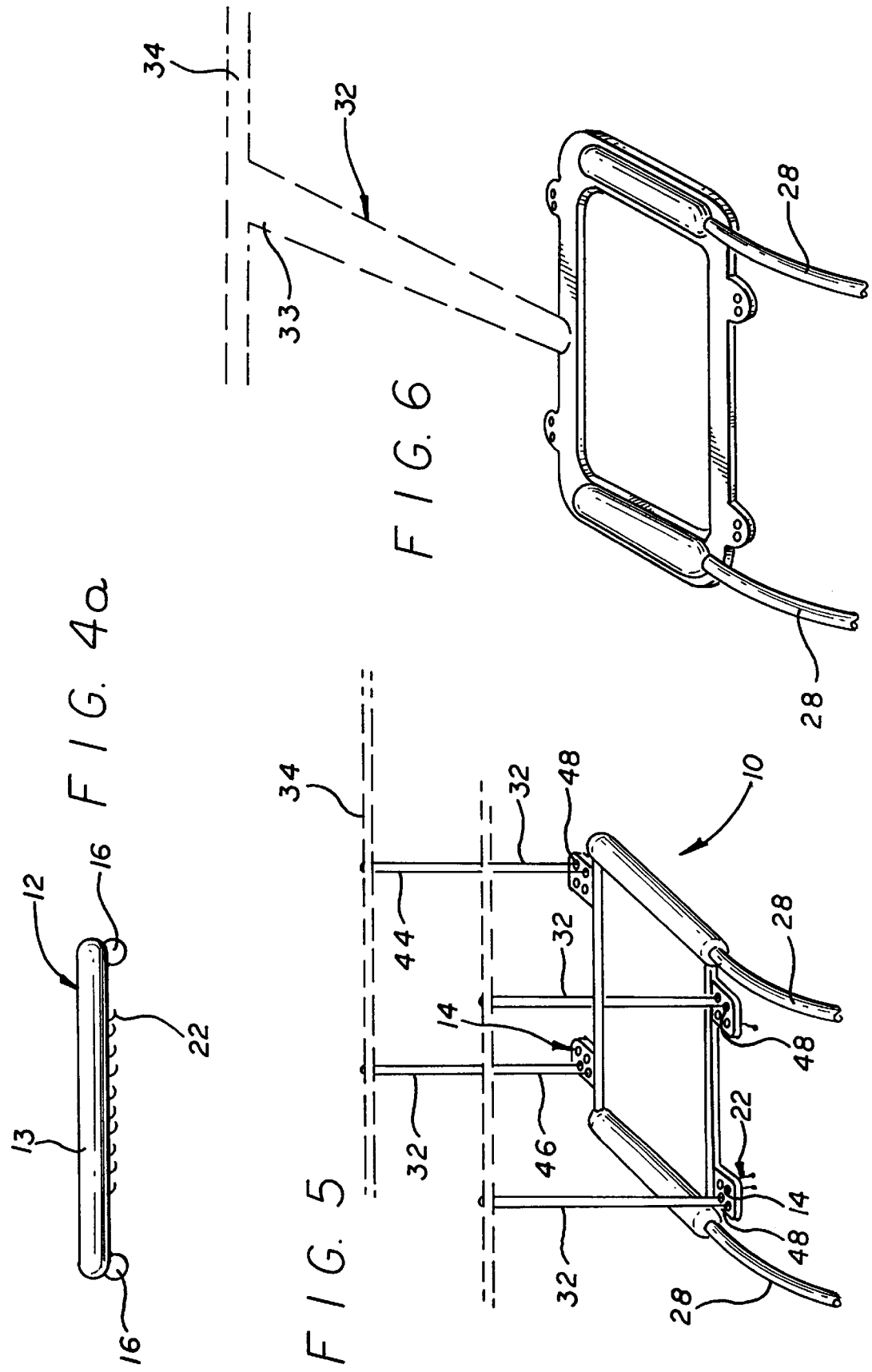

EPICARDIAL IMMOBILIZATION DEVICE

BACKGROUND OF THE INVENTION

1. Field of the Invention

This invention generally relates to devices used and methods employed in connection with surgical procedures affecting the heart and, more specifically, relates to an epicardial immobilization device and method of use, the principal purpose of both being to reduce the movement of, or to immobilize, a region of the cardiac epicardium during surgery to permit the heart to be operated on while it is beating.

2. Description of the Related Art

Surgical treatment and repair of vital organs, especially of the heart, requires a high degree of precision on the part of the physician and surgical team, and such precision heretofore has been difficult to achieve when the organ is functioning, because movement of the organ can compromise the accuracy and relative safety with which an operation successfully can be accomplished. Accordingly, and with respect to cardiac cases in particular, it has been conventional to temporarily stop the heart from functioning to effectively immobilize it while an operation is being performed. Most commonly, this is accomplished by diverting blood flow to the heart through the use of an external pump, such as with a device referred to as a "heart-lung machine," which is intended to substitute for the function of the organ so that blood can be sufficiently oxygenated and circulated through the body during surgery. The heart thus effectively will be immobilized, and the physician and the surgical team can render treatment on particular parts of the heart, or the vessels supplying or leading to or from it, with greater precision than would be possible if the heart were beating.

Clearly, though, it easily is appreciated that diverting the function of a vital organ to an artificial mechanical substitute can entail significant trauma under any circumstances and, depending on the overall condition of a particular patient, the prospect of such trauma can be such as to contraindicate life-sustaining or quality-of-life-enhancing treatment. Thus, there has been an effort to develop surgical techniques which obviate the need to resort to a heart-lung replacement pump, so as to allow an operation for treatment or repair of the heart or of its associated vessels while the heart is functioning and beating. The class of patients for which such techniques have been deemed appropriate, however, has been limited by the precision implicated by a particular procedure, because of the challenges inherently presented by a beating heart. Continuous movement of the heart renders any surgical operation performed on it or its associated vessels more complicated and more difficult than would be experienced if the organ were non-functional and, hence, effectively immobilized. Accordingly, use of techniques which involve surgical treatment of a beating heart has been limited.

One device that has been employed to immobilize the beating heart during surgery comprises a supporting ring in the shape of an open "O" and having an attached rigid arm. The supporting ring includes a base provided with a plurality of vacuum cups that are connected to a pneumatic circuit. The vacuum cups, when supplied with a suctioning force, are used to temporarily secure the device to the epicardium. Experience with this device has been less than optimum, insofar as post-surgical lesions and hematomas have been detected that are associated with the areas of the epicardium to which the vacuum cups were attached. It also is of some significance that this device is relatively expensive to use.

When an object of the surgery is treatment of the vessels of the heart muscle (e.g., the coronary arteries), another complication often is encountered due to the presence in the vasculature of occlusions, such as atheromatous plates or other restrictions, that result from atherosclerosis or another disease or condition known to cause vascular obstruction. Because these vessels carry blood (except when totally occluded), blood flow through the vessels must be curtailed while the surgery is being performed, such as operations to suture venous or arterial bridges, in order to prevent obscuring the surgeon's view of the operational field.

In the past, blood flow through the vessels of interest temporarily has been prevented through the use of ligatures, sutures or clamps which, when tightened, close off the vessel. When occluded vessels, such as coronary arteries exhibiting atheromatous plates, are involved, great care must be taken in choosing the site along the vessel at which to place a ligature, suture or clamp. This is the case because, if the compression associated with the tightening of such a ligature, suture or clamp is applied to an area in the vessel that is affected by an occlusion, the tightening force can cause the occlusion to fracture. Such fracture then might result in the partial dislodgement of the occlusion when the compressing device is removed, the dislodged portions can cause further obstructions to blood flow, such as clot formation, or other problems as the portions move through the vasculature of the patient.

In an attempt to reduce the risk that the ligatures, sutures or clamps used to temporarily prevent blood flow will cause the fracture of atheromatous plates, before placing the compressing devices, surgeons have relied on palpating the vessels before the ligatures, sutures or clamps are positioned, in order to make sure that the intended site of placement is flexible rather than rigid, which would be the expected condition of the vessel if it were characterized by an occlusion. Palpation is effective for detecting plates when the plates are present in the epicardial, or outer, surface of the lumen of a vessel, but is a less effective technique when the plates are disposed in the vessel laterally. Palpation is not an especially useful method of locating plates when the same are present in the endocardial, or inner, surface of the vessel lumen.

The devices to temporarily prevent blood flow in the vasculature of interest, however, commonly have been applied to regions of the vessels that are more distal to the heart than is optimum, owing to the fact that presence of atheromatous plates is more difficult to discern in those regions.

What has been needed, then, and what heretofore has been unavailable is an apparatus and method which permit a beating heart to be held effectively immobile while a surgical operation is being performed while concurrently allowing the operating field to be kept free of obscuring blood with a reduced risk of dislodging vascular occlusions as a result of the temporary prevention of blood flow through the vessels supplying the heart. The present invention satisfies these needs.

SUMMARY OF THE INVENTION

The present invention is directed to a device and method for effectively immobilizing the heart within the confines of a particular, defined operational field during surgery while simultaneously temporarily disrupting the passage of blood through the vessel or vessels circumscribed by the operational field so defined, thus permitting surgery to be performed on the vessel(s) free of an obstructed view. A device according to the invention includes a frame provided with a plurality of anchoring means with which to anchor the device to the epicardium. When considered appropriate, and to further secure the frame to the epicardium, connections to the epicardium can be accomplished through apertures that are provided in the anchoring means, or by way of a structure affixed to the base of the frame. One or more expandable members are disposed on opposing sides of the frame, which, when inflated, prevent(s) the flow of blood through the region of the vessel or vessels in the operational field circumscribed by the frame. The frame further can be provided with means for attaching it to an auxiliary support, when enhanced immobilization of the epicardium is deemed desirable. The frame also can be characterized by an opening or outlet passage for each vessel to be repaired.

In use, the frame of the device is positioned about the vessel or vessels to be treated by surgery, and anchored by the anchoring means. When deemed advantageous, connections to the epicardium can be made by the connecting means. The expandable member(s) then is (are) inflated to temporarily occlude the target vessel or vessels at the edges of the operational field defined by the frame, so that surgery can be carried out without blood obscuring the operational field. If deemed necessary, the immobilizing effect of the frame can be augmented by connecting it to a stationary auxiliary support.

These and other features and advantages of the present invention will become apparent from the following detailed description of the preferred embodiments which, when taken in conjunction with the accompanying drawings, illustrate by way of example the principles of the invention.

BRIEF DESCRIPTION OF THE DRAWINGS

FIG. 4a is a side elevational view of the embodiment of FIG. 4, illustrating a connecting means comprising hooks:

FIG. 5 is a perspective view of an alternate embodiment of a device of the invention illustrating a plurality of attachment means for an auxiliary support (depicted schematically);

FIG. 6 is a perspective view of an alternative embodiment of a device of the invention illustrating a single attachment means for an auxiliary support (depicted schematically).

DETAILED DESCRIPTION OF THE PREFERRED EMBODIMENTS

Figure 1:
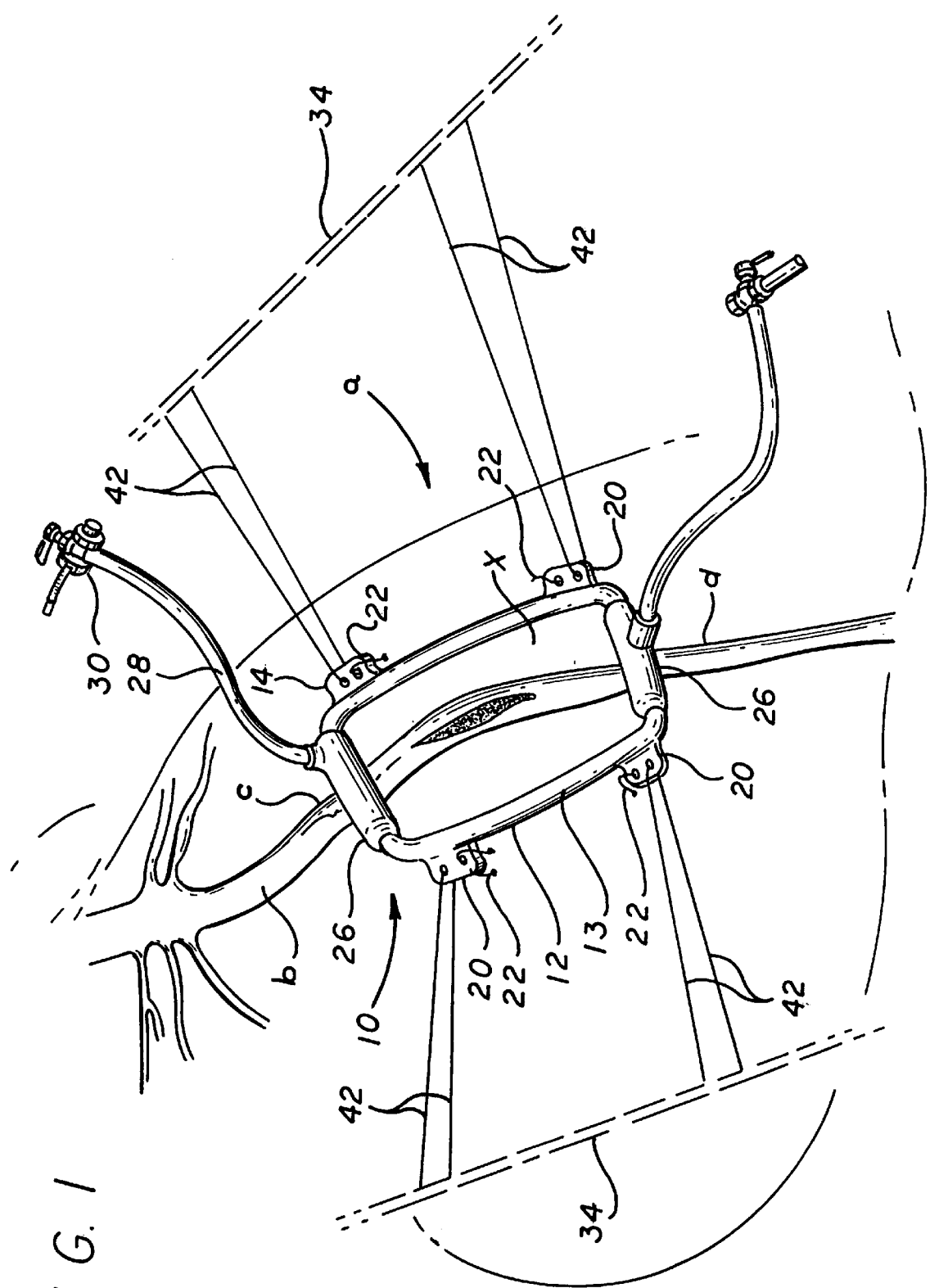
FIG. 1 is a perspective view of one embodiment of an epicardial immobilization device of the invention.

A preferred embodiment of the apparatus according to the present invention can be described by reference to FIG. 1. The epicardial immobilization device (10) comprises a substantially rectangular frame (12) formed from a malleable or flexible material, the frame having a body (13) that is provided with means (14) for anchoring the frame to the epicardium (a) and two soft expandable members (16) which, upon inflation, function to temporarily prevent blood flow in the regions of the coronary vessel or vessels (b) circumscribed by the frame. It is contemplated that the body of the frame further might be provided with one or more openings which serve as an outlet passage or outlet passages for the vessel(s) under repair.

Figure 2:
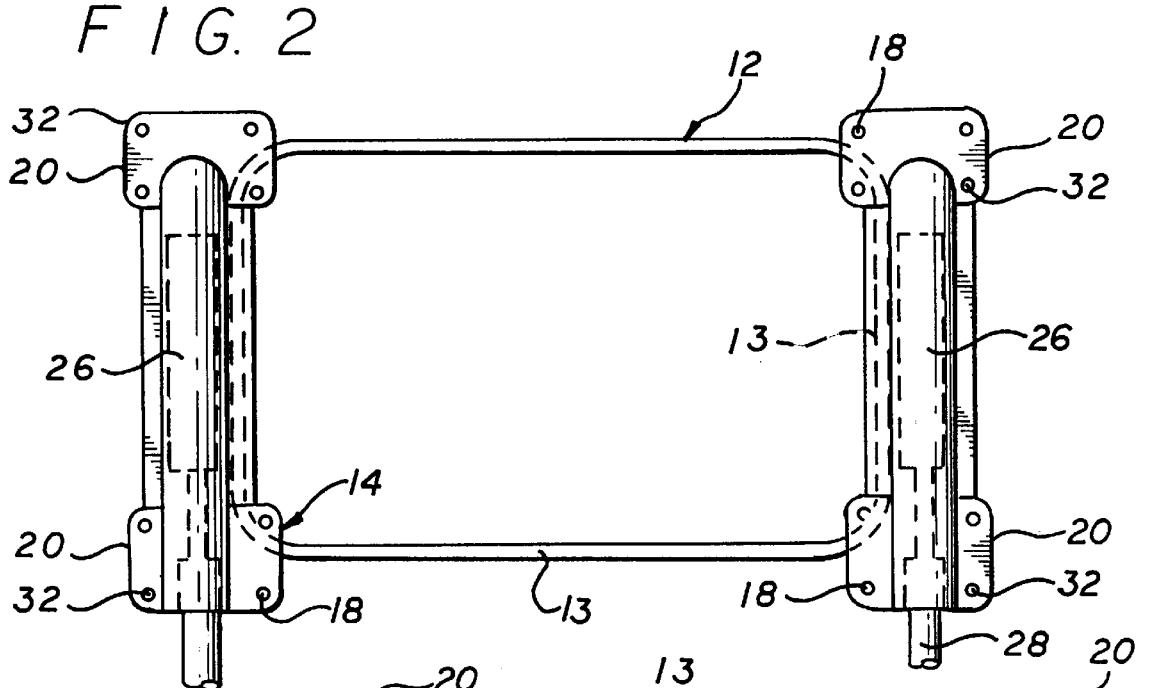
FIG. 2 is a top plan view of an alternate embodiment of the invention.
Figure 3:
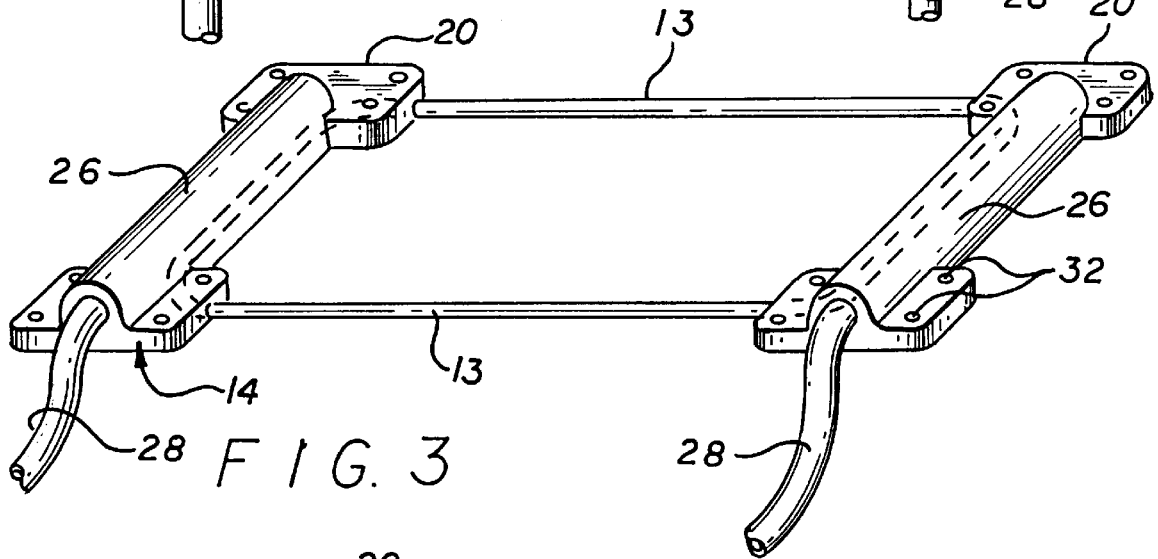
FIG. 3 is a side perspective view of the embodiment of FIG. 2.

The frame is characterized by four anchoring means (14), in the form of earlets or tabs (18) projecting outwardly from the frame, each of which earlet or tab is provided with one or more aperture(s) (20) adapted to receive connections (22) to the epicardium. The earlets or tabs (18) preferably are positioned near the four corners comprising the substantially rectangular frame (12). It is contemplated that other embodiments of the invention might be characterized by variations in the placement or configuration of the earlets or tabs (18). For example, in FIG. 2, the four earlets or tabs (18) each have two lobes, and are disposed at the four corners of the substantially rectangular frame (12). Likewise, embodiments characterized by a greater or lesser number of anchoring means (14) are envisioned, although at least three such anchoring means are deemed necessary. The embodiment illustrated in FIG. 4, for example, depicts six anchoring means (14).

Figure 4:
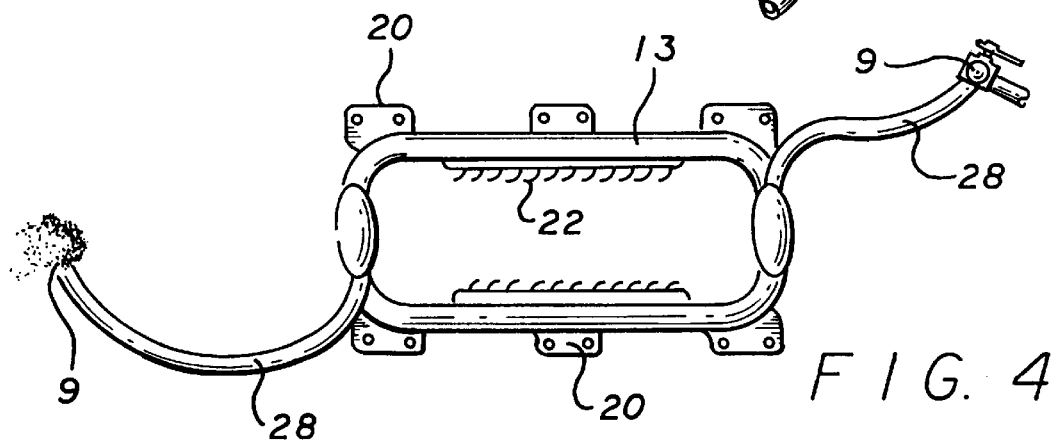
FIG. 4 is a perspective view of an alternate embodiment of the invention.

In one embodiment, and as best illustrated in FIG. 4 and 4a, epicardial connection means (22) are provided to further secure the frame to the heart. The connection means comprise a plurality of hooks (24), which extend from a supporting base. The supporting base is affixed to the body (13) of the frame (12), rather than to a particular one of the anchoring means (14).

On two of the opposing sides of the frame, expandable members (16) are mounted. Each expandable member is provided with a tubular conduit (28), which conduit is associated with an inflation valve (30).

To enhance the efficiency with which a device according to the present invention can be used in a surgical procedure, and as is best illustrated in FIG. 6, the frame (12) further is provided with means (32) for attaching the frame to an auxiliary support (34), which is held stationary in relation to the heart. The auxiliary support attachment means (32) can comprise an elongated, rigid arm (36) that projects outwardly from the frame (12) and which terminates in a connection end (38) that attaches to the auxiliary support (34).

In another embodiment according to the present invention, as illustrated in FIG. 5, the frame (12) is provided with a plurality of means (32) for attaching the frame to an auxiliary support (34). Each of these attachment means (32) has a first end (44) that can be connected to the auxiliary support (34) and a second end (46) which is affixed to the frame (12). In the embodiment illustrated in FIG. 5, the plurality of attachment means (32) are shown as tensioning threads or wires, which are affixed to the frame (12) through apertures (48) that have been provided in the earlets or tabs (18) of the frame for that purpose.

When used in a surgical procedure, the apparatus according to the invention is positioned so that the malleable or flexible frame (12) rests against the epicardium (a) of the heart, to define the operational field. The soft expandable members (16) thereby are disposed against an upper and lower occlusion zone (c, d) of the target vessel or vessels.

Optionally, the epicardial connections (22) via the associated hooks (24) or otherwise connect the frame (12) to the epicardium (a). An operational field on the beating heart thus is defined by the boundaries of the frame (12), and the epicardium (a) is tensioned and held relatively immobile in relation to the rest of the heart organ, which continues to beat throughout the procedure.

When the soft inflatable member or members (16) are inflated via the tubular conduits (28) and associated inflation valves (30), the expandable members press against the vessel or vessels extending through the operational field defined by the frame (12), thus temporarily preventing the passage of blood through the vessel or vessels in the region circumscribed by the frame. More specifically, when the expandable members are inflated, the epicardial, or outer, side of the target vessel or vessels collapses against the corresponding endocardial, or inner side. The relative softness of the balloons thus accomplishes the temporary cessation of the blood flow through the affected vasculature with far less trauma than is associated with traditional occlusion techniques (e.g., those techniques involving ligatures, sutures or clamps). Surgery to treat the vessels then can be performed, e.g., a coronary bypass operation to treat a vascular lesion.

In situations in which maximum immobilization of the operational field defined by the frame (12) is desired, the singular or plurality of auxiliary support attachment means (32) can be resorted to in order to affix the frame to an auxiliary support (34).

Following the surgery, the device according to the present invention can be cut away from the epicardium and discarded. However, and as is contemplated, if the frame (12) further is provided with an opening or outlet passage for each repaired vessel, not only can the frame be removed without cutting, but it can be preserved intact for potential future uses in other procedures.

While a particular form of the invention has been illustrated and described, it will also be apparent to those skilled in the art that various modifications can be made without departing from the scope of the invention. Accordingly, it is not intended that the invention be limited except by the appended claims.

What is claimed is:

1. A device for effectively immobilizing the epicardium of the heart in a specific operational field and for keeping the field free of obscuring blood flow during surgery, the device comprising:
   a frame for defining an operational field, said frame having a body to which are attached a plurality of anchoring means adapted to anchor said frame to the epicardium, said body having a top surface and, opposite the top surface, a bottom surface adapted to contact the epicardium; and
   a first expandable member disposed on a first side of said frame, said first expandable member adapted to be connected to an inflation source;
   wherein said frame is adapted to be secured to the epicardial surface by way of said anchoring means, and the operational field can be kept free of blood flow during surgery by inflating said first expandable member to temporarily stop the passage of blood through portions of vessels within the field defined by the frame.

2. The device of claim 1, further including a second expandable member disposed on a second side of said frame, said second expandable member adapted to be connected to an inflation source.

3. The device of claim 1, wherein said frame is formed from a flexible material.

4. The device of claim 1, wherein said frame is substantially rectangular in shape.

5. The device of claim 1, wherein the plurality of anchoring means comprises at least three anchoring means.

6. The device of claim 5, wherein said plurality of anchoring means comprises four anchoring means.

7. The device of claim 5, wherein said plurality of anchoring means comprises four anchoring means and each anchoring means is disposed approximately at a corner of said substantially rectangular frame.

8. The device of claim 1, wherein said plurality of anchoring means comprises six anchoring means.

9. The device of claim 1, wherein each of said plurality of anchoring means is spaced approximately equidistantly from every adjacent one of said plurality of anchoring means.

10. The device of claim 1, wherein each of said plurality of anchoring means is in the shape of an earlet.

11. The device of claim 1, further including connecting means adapted to connect said frame to the epicardium.

12. The device of claim 11, wherein said connecting means comprises a plurality of hooks attached to said bottom surface of said body of said frame.

13. The device of claim 11, wherein each of said anchoring means is in the shape of an earlet and each said earlet is provided with an aperture adapted to receive said connecting means.

14. The device of claim 13, wherein each said earlet further is provided with attachment means adapted to affix said frame to an auxiliary support.

15. The device of claim 14, wherein said attachment means comprises tensioning wires.

16. The device of claim 1, wherein said body of said frame is provided with attachment means adapted to attach said frame to an auxiliary support.

17. The device of claim 16, wherein said attachment means comprises a rigid arm that projects outwardly from said frame.

18. The device of claim 1, wherein said connecting means is disposed on a base of said body of said frame.

19. The device of claim 1, wherein said body of said frame further is provided with at least one opening, said at least one opening providing an outlet passage for a vessel under repair.

20. A method for effectively immobilizing the epicardium of the heart in a specific operational field and for keeping the field free of obscuring blood flow during surgery, employing a device having a frame including a plurality of anchoring means adapted to anchor the frame to the epicardium and at least one expandable member, disposed on the frame, which is adapted to be connected to an inflation source, the method comprising the steps of:
   (a) positioning the frame so that the frame is anchored to the epicardium by the anchoring means;
   (b) connecting the at least one expandable member to an inflation source; and
   (c) inflating the expandable member to temporarily stop the passage of blood through the portion of the vasculature to be treated by the surgical procedure.

21. The method of claim 20, further comprising the step of attaching the frame to an auxiliary support, to enhance the immobilization of the epicardium.

22. A method for effectively immobilizing the epicardium of the heart in a specific operational field and for keeping the field free of obscuring blood flow during surgery, employing a device having a frame including a plurality of anchoring means adapted to anchor the frame to the epicardium, connecting means adapted to connect the frame to the epicardium, and at least one expandable member, disposed on the frame, which is adapted to be connected to an inflation source, the method comprising the steps of:
   (a) positioning the frame so that the frame rests against the epicardium;
   (b) connecting the frame to the epicardium with the connecting means;

(c) connecting the at least one expandable member to an inflation source; and (d) inflating the expandable member to temporarily stop the passage of blood through the portion of the vasculature to be treated by the surgical procedure.

23. The method of claim 22, further comprising the step of attaching the frame to an auxiliary support, to enhance the immobilization of the epicardium.

* * * * *